(12) United States Patent
Ferro et al.

(10) Patent No.: US 10,368,882 B2
(45) Date of Patent: Aug. 6, 2019

(54) BONE REMOVING DEVICE

(71) Applicant: AOD Holdings, LLC, Arroyo Grande, CA (US)

(72) Inventors: Thomas Ferro, Arroyo Grande, CA (US); Austin T. Ferro, Arroyo Grande, CA (US); Joseph R. Phillips, Paso Robles, CA (US)

(73) Assignee: AOD Holdings, LLC, Arroyo Grande, CA (US)

( * ) Notice: Subject to any disclaimer, the term of this patent is extended or adjusted under 35 U.S.C. 154(b) by 140 days.

(21) Appl. No.: 15/431,592

(22) Filed: Feb. 13, 2017

(65) Prior Publication Data
US 2018/0228500 A1 Aug. 16, 2018

(51) Int. Cl.
*A61B 17/16* (2006.01)
*A61B 17/14* (2006.01)
*A61B 17/00* (2006.01)

(52) U.S. Cl.
CPC ...... *A61B 17/1659* (2013.01); *A61B 17/1675* (2013.01); *A61B 17/142* (2016.11); *A61B 17/1631* (2013.01); *A61B 2017/0046* (2013.01)

(58) Field of Classification Search
CPC ................. A61B 17/1659; A61B 17/1675
See application file for complete search history.

(56) References Cited

U.S. PATENT DOCUMENTS

| | | | | |
|---|---|---|---|---|
| 7,955,337 B2* | 6/2011 | Lee | ..................... | A61B 17/1659 606/85 |
| 8,002,776 B2* | 8/2011 | Liu | ..................... | A61B 17/1659 606/85 |
| 8,273,088 B2* | 9/2012 | Zalenski | ............ | A61B 17/1659 606/279 |
| 8,444,648 B2* | 5/2013 | Del Rio | ............. | A61B 17/1624 606/85 |

* cited by examiner

*Primary Examiner* — Nicholas W Woodall (57) ABSTRACT

A bone removing device. The device includes a gearing mechanism and a bone removing device housing containing the gearing mechanism. A first non-oscillating surface is operably connected to the gearing mechanism and a first oscillating rasping surface is operably connected to the gearing mechanism. When the gearing mechanism of the bone removing device is operated, the first oscillating rasping surface is oscillated. The first non-oscillating surface may comprise a rasping surface.

20 Claims, 6 Drawing Sheets

BONE REMOVING DEVICE

FIELD OF THE PRESENT DISCLOSURE

This present disclosure relates to surgical bone removing system and components. More specifically, the present disclosure relates to a bone removing device and methods for use during knee replacement surgery, such as a total knee replacement or a unicompartmental knee replacement (also called "partial" knee replacement) wherein only a portion of the knee is resurfaced.

BACKGROUND

Oftentimes, it may become necessary to initiate corrective surgery on a particular knee joint of a patient. As just one example, partial and total knee arthroplasty (or total knee replacement) is a surgical procedure in which parts of the knee joint are replaced with artificial parts (prostheses). During the corrective surgery, the worn out bone and cartilage is removed and replaced with various biocompatible implants that take the place of the resected bone and cartilage. Knee arthroplasty usually comprises of (i) a femoral component which is fixed onto the distal end of the femur, (ii) the tibial components, which comprise a tibial tray and an intermediate component usually made from ultra-high molecular weight polyethylene (UHMWPE).

In order to properly place these components, precise resection of the bone needs to be made by the surgeon. Resections to both the femoral condyles and tibia need to be made so that the implants precisely replace the material removed.

There is, therefore, a general need for a bone removal system and/or methods that enable surgeons to provide for precise bone resections. There is also a general need for bone removal devices and/or methods that allow a surgeon to maintain accuracy and precision in the cutting of the measured section of the bone during an orthopedic surgery. There is also a need for a bone removing device that allows surgeons to fine tune adjustments in the bone resection. There is also a general need for a bone removing device and/or system that enables a surgeon to remove minor layers of bone to facilitate proper gap balancing and placement of the implants.

SUMMARY

In one arrangement, a bone removing device comprises a gearing mechanism, a bone removing device housing containing the gearing mechanism, a first non-oscillating surface operably connected to the gearing mechanism, and a first oscillating rasping surface operably connected to the gearing mechanism. In this arrangement, when the gearing mechanism of the bone removing device is operated, the first oscillating rasping surface is oscillated.

In one bone removing device arrangement, a distance between the first non-oscillating surface and the first oscillating rasping surface comprises an adjustable distance. In one bone removing device arrangement, the adjustable distance between the first non-oscillating surface and the first oscillating rasping surface comprises a manually adjustable distance. In one bone removing device arrangement, the bone removing device comprises a manually operated height adjuster for adjusting the manually adjustable distance between the first non-oscillating surface and the first oscillating rasping surface. In one bone removing device arrangement, the manually operated height adjuster comprises a twistable outer housing comprising geared teeth on a first end, wherein the geared teeth are configured to operate a rack and pinion mechanism so as to spread the distance between the non-oscillating surface and the oscillating rasping surface.

In one bone removing device arrangement, a proximal end of the bone removing device housing is adapted to receive a surgical instrument. In one bone removing device arrangement, the surgical instrument comprises a rotating surgical instrument. In one bone removing device arrangement, the rotating surgical instrument is configured to rotate a main drive shaft contained within the bone removing device housing. In one bone removing device arrangement, the main drive shaft is connected to a planetary drive system.

In one bone removing device arrangement, the bone removing device further comprises a sun gear. The planetary drive is configured to provide a ratio between the sun gear and the main planetary gear in order to increase revolutions per minute created by the rotating surgical instrument.

In one bone removing device arrangement, the bone removing device further comprises an intermediate housing. The intermediate housing containing a vertical beveled gear and a horizontal beveled gear. The vertical beveled gear and the horizontal beveled gear are configured to translate a rotational motion into an oscillating linear motion of the first oscillating rasping surface. In one bone removing device arrangement, the horizontal beveled gear comprises a protruding peg that engages an oscillating drive shaft. For example, the protruding peg may engage a slot defined by the oscillating drive shaft.

In one bone removing device arrangement, the oscillating drive shaft is detachably connected to the first oscillating rasping surface. In one bone removing device arrangement, the first oscillating rasping surface is removably seated within a cavity defined by a main chassis.

In one bone removing device arrangement, the first non-oscillating surface comprises an adjustable non-oscillating surface.

In one bone removing device arrangement, the bone removing device comprises a height adjustment knob comprising a geared face. In one bone removing device arrangement, the bone removing device further comprises a spur gear, wherein the geared face of the height adjustment knob engages the spur gear. Rotation of the height adjustment knob adjusts a distance between the first non-oscillating surface, and the first oscillating rasping surface. In one arrangement, rotation of the height adjustment knob adjusts a distance between a top surface of the first non-oscillating surface and a bottom surface of the first oscillating rasping surface.

In one bone removing device arrangement, the bone removing device further comprises a worm gear drive that is connected to the spur gear. The geared face of the height adjustment knob engages the spur gear and rotation of the height adjustment knob adjusts a distance between the first non-oscillating surface, and the first oscillating rasping surface.

In one bone removing device arrangement, the first oscillating rasping surface operably connected to the bone removing device housing comprises a plurality of teeth. In one bone removing device arrangement, a height of the plurality of teeth is uniform.

In one bone removing device arrangement, the bone removing device comprises a second non-oscillating surface operably connected to the gearing mechanism, and a second oscillating rasping surfaces operably connected to the gearing mechanism, wherein, when the bone removing device is operated, the first and the second oscillating rasping surfaces are oscillated.

In one bone removing device arrangement, the first non-oscillating surface comprises a rasping surface.

The foregoing summary is illustrative only and is not intended to be in any way limiting. In addition to the illustrative aspects, embodiments, and features described above, further aspects, embodiments, and features will become apparent by reference to the figures and the following detailed description.

BRIEF DESCRIPTION OF THE DRAWINGS

Exemplary arrangements are described herein with reference to the drawings, in which.

DETAILED DESCRIPTION

In the following detailed description, reference is made to the accompanying drawings, which form a part hereof. In the drawings, similar symbols typically identify similar components, unless context dictates otherwise. The illustrative arrangements described in the detailed description, drawings, and claims are not meant to be limiting. Other arrangements may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present disclosure relates to techniques and apparatus for partial or total knee arthroplasty surgery by utilizing a bone removing device that allows surgeons to create fine tune adjustments in the resection. By utilizing the presently disclosed devices and methods, a surgeon will be able to remove minor layers of bone so as to facilitate proper gap balancing and placement of the implants.

Figure 1:
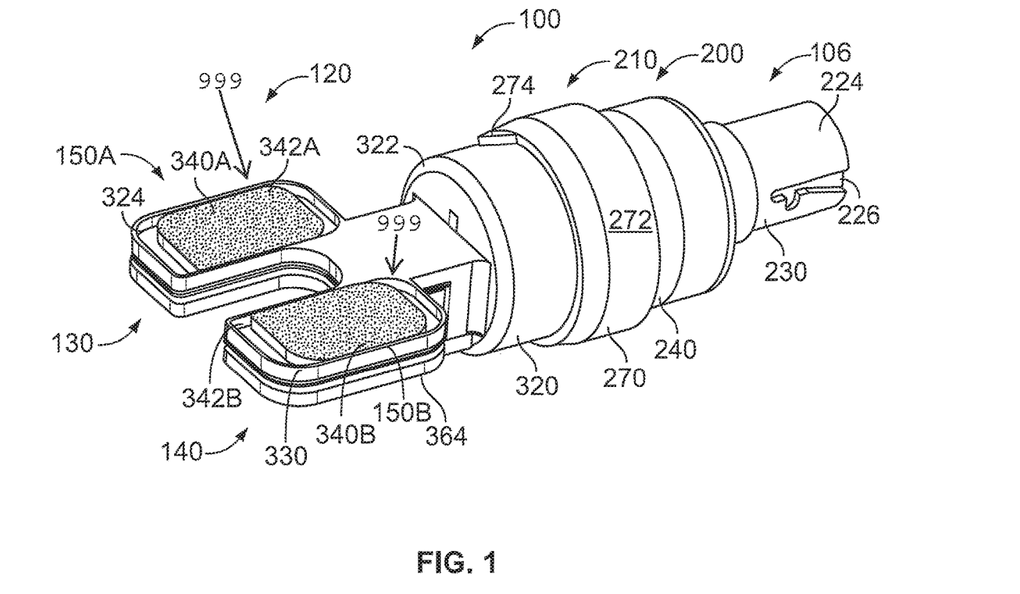
FIG. 1 illustrates a perspective view of a bone removing device arrangement.

For example, FIG. 1 illustrates a perspective view of an arrangement of a bone removing device 100. In this preferred bone removing device arrangement, the bone removing device 100 comprises a connecting element or main adaptor end 220 at a proximal end 106 of the bone removing device 100. Such a connecting element or main adaptor end 220 allows the bone removing device 100 to be removably adapted to a surgical tool. Such a surgical tool may comprise a powered surgical drill. Alternative surgical tools may also be used.

The bone removing tool 100 comprises a bone removing device housing 210. In one preferred housing arrangement, the device housing 210 comprises multiple housing component parts. The bone removing device housing 201 is configured to contain a gearing mechanism 200. Preferably, this gearing mechanism 200 translates a rotation power generated by a surgical tool coupled to the main adaptor end 220 of the bone removing device 100 so as to generate an oscillating linear translation motion. In one arrangement, the oscillating linear translation motion is used to oscillate a bone removing surface, such as one or more rasping elements 340 A,B. A bone removing surface of the one or more rasping elements 340 A,B rasp may comprise a plurality of teeth 999. The one or more rasping elements 340 A,B are preferably detachably connected to a main drive shaft of the bone removing device 100. In one arrangement, the plurality of teeth 999 of the rasping elements 340 A,B comprise a height that may vary. This allows the bone removing device to adjust the height of each condyle of the femur in a total knee arthroplasty.

In order to accommodate the varying heights of bone resection in reference to the tibal plateau, as will be described herein in detail, the bone removing device 100 is able to adjust a bone removal distance ($D_{BRD}$) or height via, for example, an internal rack and pinion geared mechanism. Alternative height adjusting mechanisms may be used to adjust this height between a lower surface of a bottom paddle and a top surface of the rasping elements 340A,B. To prevent an operator of the bone removing device 100 from setting the height of the device in an undesired position, the bone removing device 100 may also comprise feed back features, such as visual indicators, tactile or audio feedback features via clicks to represent a certain height. As such, the bone removing device 100 will help improve gap balancing of knee implants.

In this particular illustrated arrangement, the bone removing device 100 may be used during a total knee replacement procedure since the device 100 includes a first oscillating rasping surface and a second oscillating rasping surface. However, in an alternative arrangement (FIGS. 7-9), the bone removing device 560 may be used during a unicompartmental knee arthroplasty as the illustrated bone removing device 560 comprises a single oscillating rasping element 740A comprising a single rasping surface 742A.

Returning to FIG. 1, as illustrated, the bone removing device 100 comprises a main adaptor end 220, an intermediate body 240, a height adjustment knob 270, and a main rasp chassis 320. The main adaptor end 220 is provided near a proximal end 106 of the bone removing device 100. Preferably, the main adaptor end 220 is configured to be removably connected to a powered surgical tool such as a powered surgical drill. As just one example, the main adaptor end 220 may be provided with an engageable a key way 226 provided along an outer surface 224. Alternatively, the main adaptor end 220 may be configured adapt to other types of surgical tools, such as an oscillating saw and reciprocating saw.

The bone removing device 100 further comprises an intermediate body 240 that is provided between the main adaptor end 220 and a height adjustment knob 270. As will be explained in greater detail herein, the height adjustment knob 270 comprises a rotatable height adjustment knob and may also comprise an indicator 274 that is provided along an outer surface 272 of the height adjustment knob 270. Rotation of the adjustment knob 270 will adjust a bone removing height defined by a distance between a top surface 342A,B of the rasping elements 342A,B and a bottom surface 364 of the adjustable height paddle 360.

Figure 2:
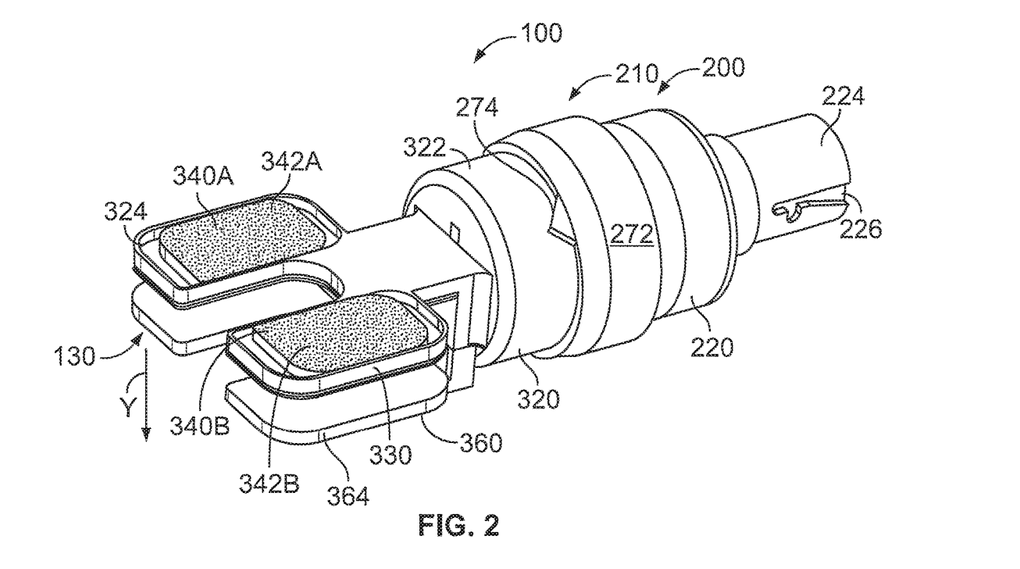
FIG. 2 illustrates a perspective view of the bone removing device arrangement illustrated in FIG. 1 after rotation of a height adjustment knob.

For example, FIG. 2 is a perspective view of the bone removing device 100 arrangement illustrated in FIG. 1 after rotation of the height adjustment knob 270. Specifically, in this illustrated arrangement, the height adjustment knob 270 and hence the adjustment knob indicator 274 has been rotated in a counter clock wise direction, as seen from the proximal end 106 of the bone removing device 100. Based in part on a gearing provided between the height adjustment knob 270 and the main rasp chassis 320, rotation of the height adjustment knob 270 moves the adjustable height paddle 360 in the Y-direction as noted in FIG. 2, away from the rasping elements 340A,B. As such, there is now a bone removal distance $D_{BRD}$ that may be defined between the top surface 342A,B of the rasping elements 340A,B and the bottom surface 364 of the adjustable height paddle 360. (See, e.g., FIG. 4)

One advantage of the bone removing device 100 illustrated in FIGS. 1 and 2 is ability of a user of the device 100 to specifically identify and adjust bone removal distance $D_{BRD}$ so as to achieve a specific height and therefore the degree of bone removal during an anthroplasty procedure.

The bone removing device 100 further comprises a main rasp chassis 320. In this illustrated arrangement, the main rasp chassis 320 comprises a main body portion 322 and also comprises a first and a second main rasp chassis arm 324, 330, respectively. The main body 322 of the main rasp chassis 320 is operatively coupled to a distal end of the height adjustment knob 270. Both the first and the second chassis arms 324, 330 extend in a distal direction, away from the main rasp chassis body portion 322. Each arm 324, 330 defines a rasp element receiving cavity. For example, as illustrated in FIGS. 1 and 2, the first chassis arm 324 of the main rasp chassis 320 defines a first rasping element receiving cavity 326. It is this first cavity 326 that receives a first rasping element or a first oscillating rasping 340A. The top surface of the first rasping element 340A comprises a first oscillating rasping surface 342A that is oscillated by the bone removing device 100 so as to remove an undesired amount of bone that comes into contact with the first oscillating rasping surface 324A.

Similarly, the second arm 330 of the main rasp chassis 320 defines a second rasping element receiving cavity 336. It is this second rasp receiving cavity 336 that receives a second rasping element 340B. The top surface of the second rasping element comprises a second oscillating rasping surface 342B that is oscillated by the bone removing device 100. Oscillation of the second oscillating rasping surface 342B removes an undesired amount of bone that comes into contact with the second oscillating rasping surface 324B.

Figure 3:
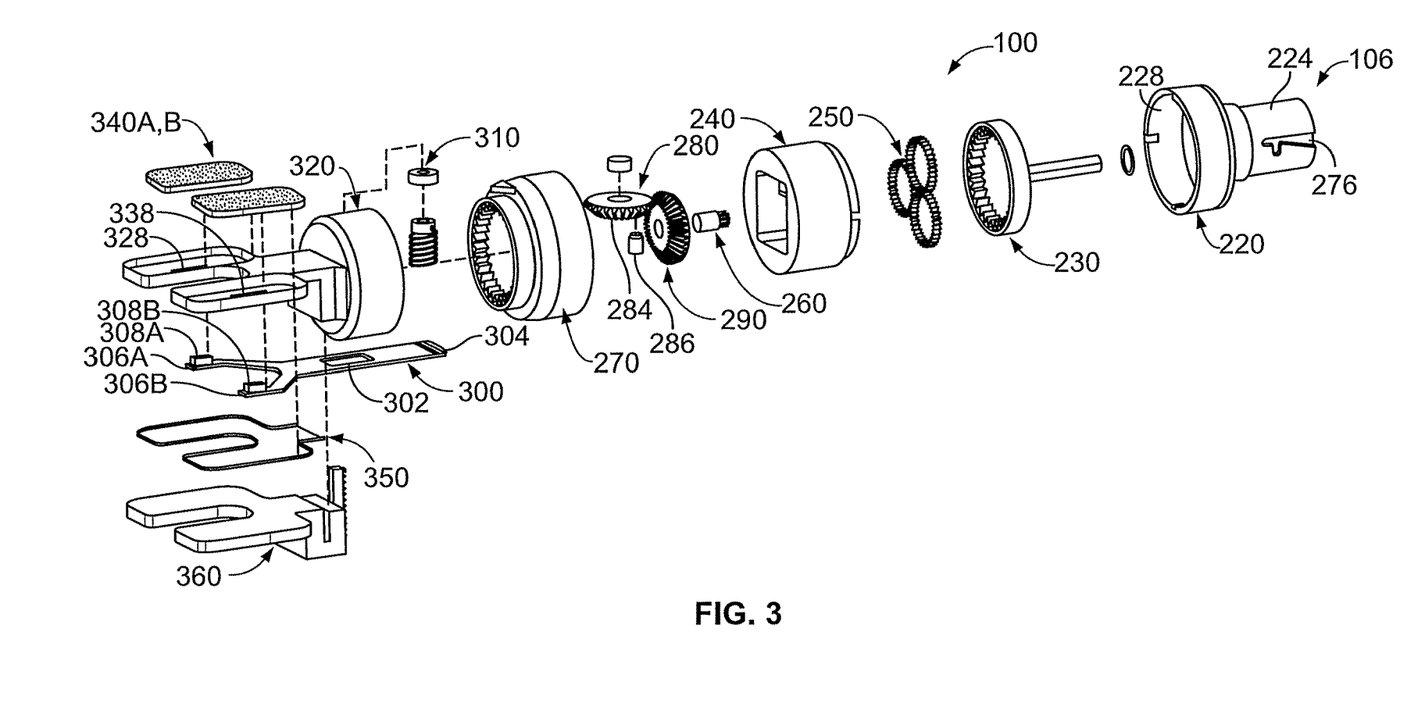
FIG. 3 illustrates an exploded view of the bone removing device arrangement illustrated in FIGS. 1 and 2.
Figure 4:
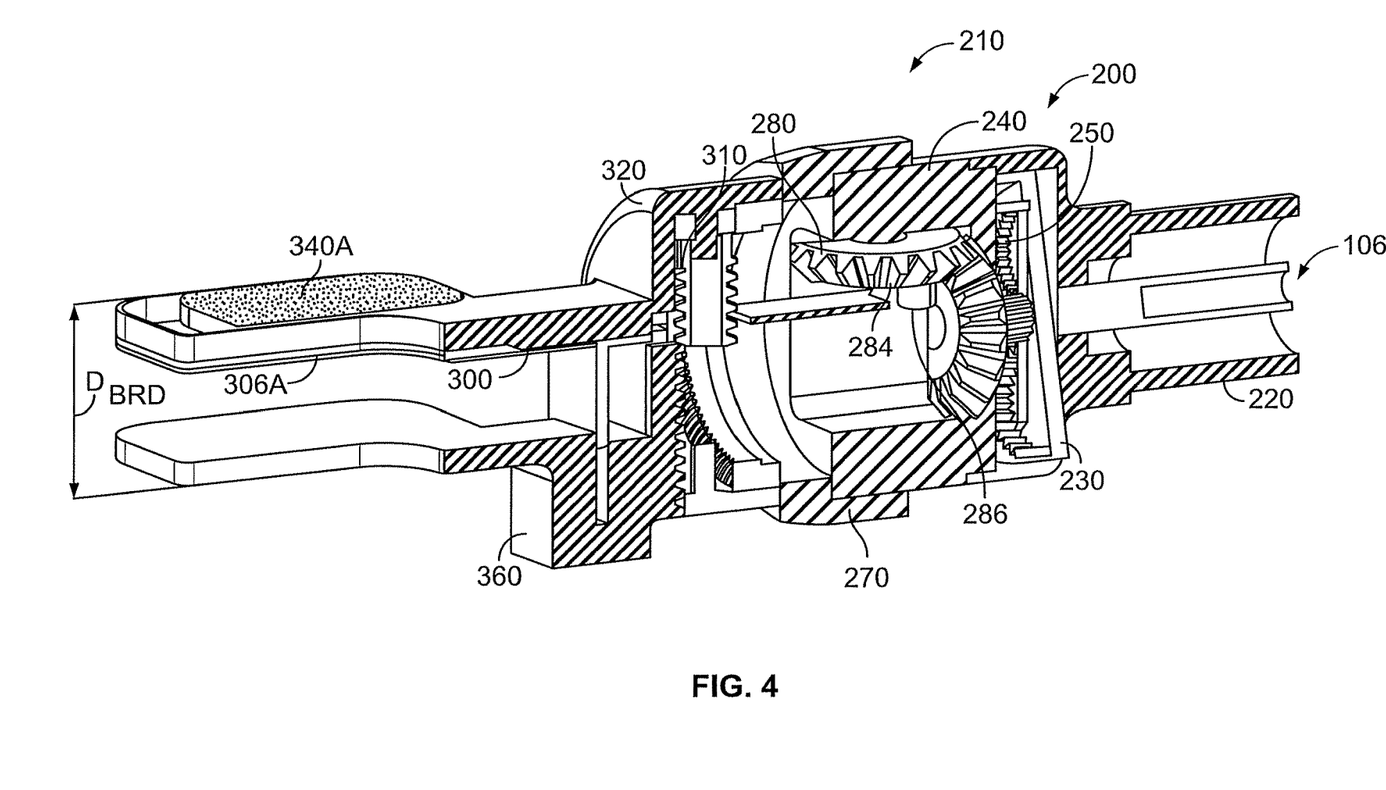
FIG. 4 illustrates a cross sectional view of the bone removing device arrangement illustrated in FIG. 2.

FIG. 3 illustrates an exploded view of the bone removing device 100 illustrated in FIGS. 1 and 2. FIG. 4 illustrates a cross sectional view of the device illustrated in FIG. 3. Now referring to both FIGS. 3 and 4, the main adaptor end 220 is configured to operatively engage with powered surgical instrument, such as a powered drill. Once the powered surgical device is engaged with the main adaptor end 220, the powered surgical device will rotate the main drive shaft 230 which is positioned inside a inner cavity 228 defined by the main adaptor end 220. The main drive shaft 230 is operatively coupled to a planetary drive sleeve system 250.

The purpose of the planetary drive system 250 is to provide a ratio between a sun gear 260 and the main planetary gear 250 so as to increase the overall revolutions per minute that is created by the powered surgical instrument.

The planetary drive system 250 resides between the main drive shaft 230 and the intermediate body 240. An internal cavity 246 defined by the intermediate body 240 houses a horizontal beveled gear 280 and a vertical beveled gear 290. The horizontal beveled gear 280 and the vertical beveled gear 290 allows the gearing mechanism 200 of the bone removing device 100 to translate the rotational motion created by the main drive shaft 230 into an oscillating linear motion. It is this oscillating linear motion that is used so as to oscillate the oscillating drive shaft 300, and hence the first and second rasping elements 340A, B.

In order to generate this oscillating linear motion, the gearing mechanism 200 further comprises a protruding peg 286 that extends from a bottom surface 284 of the horizontal beveled gear 280. This protruding peg engages with a slot 304 that is provided near a proximal end of the oscillating drive shaft 300. The horizontal gear 280 and the oscillating drive shaft 300 work based upon a scotch yoke mechanism, also known as a slotted link mechanism. With such a mechanism, the horizontal gear 286 and the protruding peg 286 work together so as to allow for the conversion of the rotational motion of the rotating horizontal bevel gear 280 to the linear, oscillating motion of oscillating drive shaft 300.

The distal end of the oscillating drive shaft 300 comprises two oscillating drive shaft arms 306A, B. Each oscillating drive shaft arm 306A, B comprises a vertically oriented connection member 308A, B, respectively. For example, the first drive shaft arm 306A comprises a first vertically oriented connection member 308A and the second drive shaft arm 306B comprises a second vertically oriented connection member 308B. The vertically extending connection members 308A, B are configured to extend away from the each respective arm 306A, B and extend vertically through a slot defined by the first and second main rasping chassis arm cavities 326, 336, respectively. For example, the first vertically extending connection member 308A extends vertically through a first arm cavity slot 328 and is removably connected to the first rasping element 340A. The second vertically extending connection member 308B is similarly configured to the second rasping element 340B.

In this manner, when the oscillating drive shaft 300 is oscillated and since the oscillating drive shaft arms 306A, B are now operatively coupled to respective rasping elements 340A, B, the rasping elements 340A, B are now also oscillated within the rasping element cavities 326, 336 as the connection elements 308A, B are oscillate back and forth within the slots 328, 338 defined by the first and second cavities 326, 336.

In order to protect the user of the bone removing device 100 from the oscillating motion of the oscillating drive shaft 300, a dampening mechanism 350 (e.g., a casing) can be press fit into to a bottom surface of the main rasp chassis 320.

The adjustable height paddle 360 is movably engaged with the main rasp chassis 320. The height of the adjustable height paddle 360 can be adjusted via the height adjustment knob 270 as herein discussed. A front surface of the height adjustment knob 270 comprises a geared front surface. This geared front surface is threadedly engaged with a spur gear 310 that is in threaded engagement with a threaded portion of the adjustable height paddle 360. The spur gear 310 is connected to a worm gear drive which is able to act upon and therefore move the adjustable height paddle 360.

Figure 5:
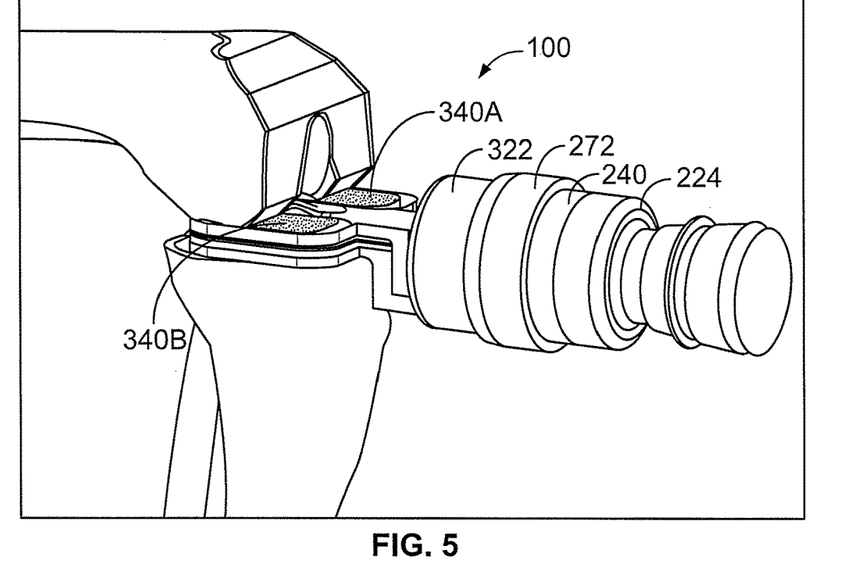
FIG. 5 illustrates a perspective view of the bone removing device arrangement illustrated in FIGS. 1-4 engaged with a resected bone.
Figure 6:
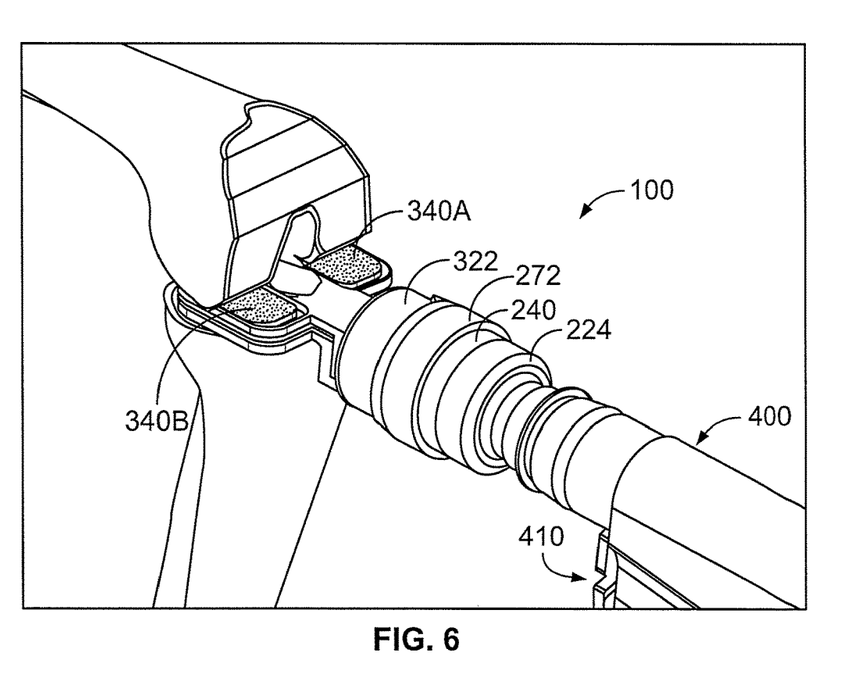
FIG. 6 illustrates a perspective view of the bone removing device arrangement illustrated in FIG. 5 with a surgical tool attached.

FIG. 5 illustrates a perspective view of the bone removing device 100 illustrated in FIGS. 1-4 engaged with a resected bone. FIG. 6 illustrates a perspective view of the bone removing device 100 illustrated in FIG. 5 with a surgical tool 400 attached. As illustrated, the surgical tool 400 may comprise certain human interface devices 410 that allow a user to operate the bone removing device 100, such as turning on and off the surgical tool. The human interface devices 410 may also be used to adjust the speed of oscillation of the rasping elements 340A, B.

Figure 7:
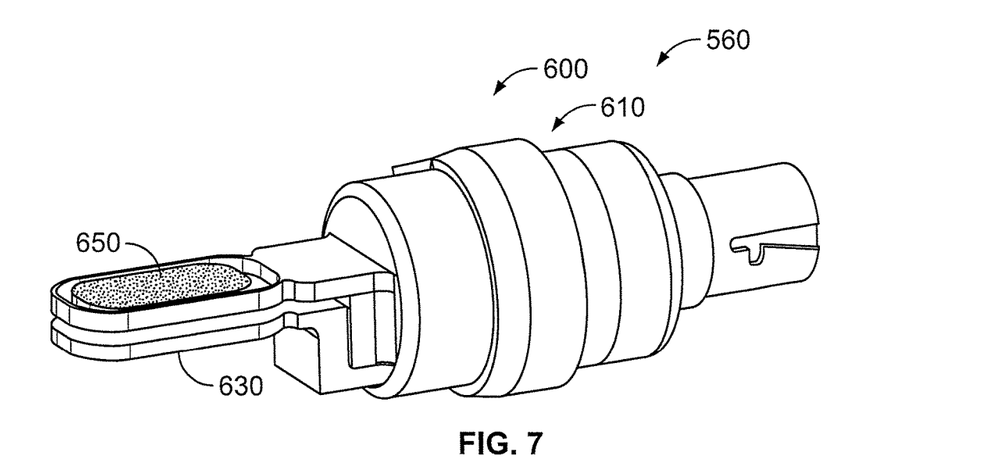
FIG. 7 illustrates a perspective view of an alternative bone removing device arrangement.
Figure 8:
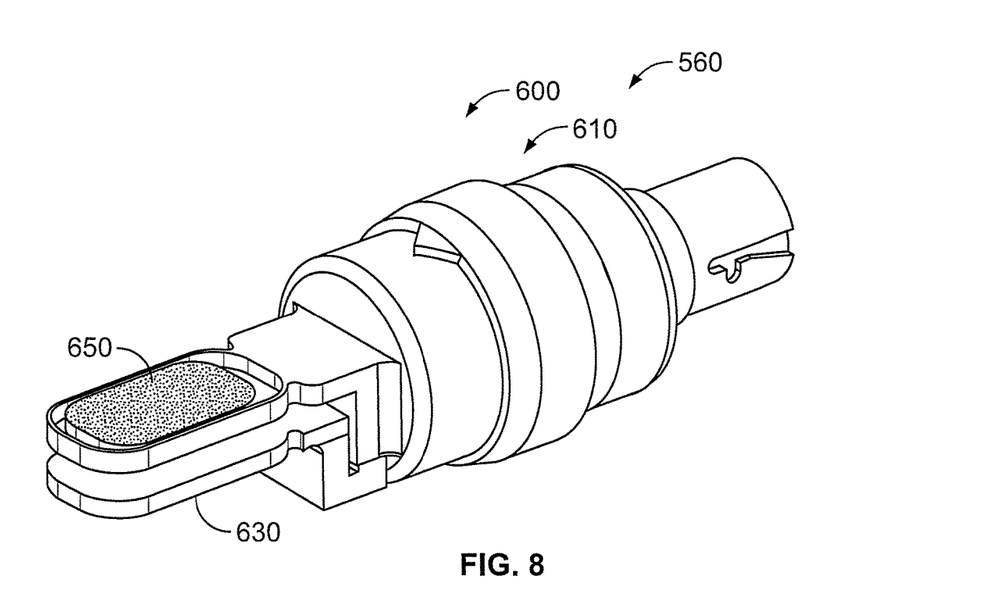
FIG. 8 a perspective view of the bone removing device arrangement illustrated in FIG. 7 after rotation of a height adjustment knob.

FIG. 7 illustrates another arrangement for a bone removing device 560 that operates in a similar fashion as the bone removing device 100 illustrated in FIGS. 1-4. FIG. 8 illustrates the bone removing device 560 illustrated in in FIG. 7 but with a height generated between a top surface of a first oscillating rasping surface 650 and a bottom surface of a first non-oscillating surface 630.

In this illustrated arrangement, the bone removing device 650 comprises similar components as the first bone removing device arrangement 100 illustrated in FIGS. 1-4. For example, in the arrangement illustrated in FIGS. 7-8, the bone removing device 560 comprises a gearing mechanism 600 and a bone removing device housing 610 containing the gearing mechanism 600. A first non-oscillating surface 630 is operably connected to the gearing mechanism 600. A first oscillating rasping surface 650 is also operably connected to the gearing mechanism 600. In this arrangement, when the gearing mechanism 600 of the bone removing device 560 is operated, the first oscillating rasping surface 650 is oscillated. In a preferred arrangement, the gearing mechanism 600 is similar to the gearing mechanism 200 discussed with respect to FIGS. 1-4. In addition, the bone removing device housing 610 is similar to the bone removing device housing 210 discussed with respect to FIGS. 1-4.

Figure 9:
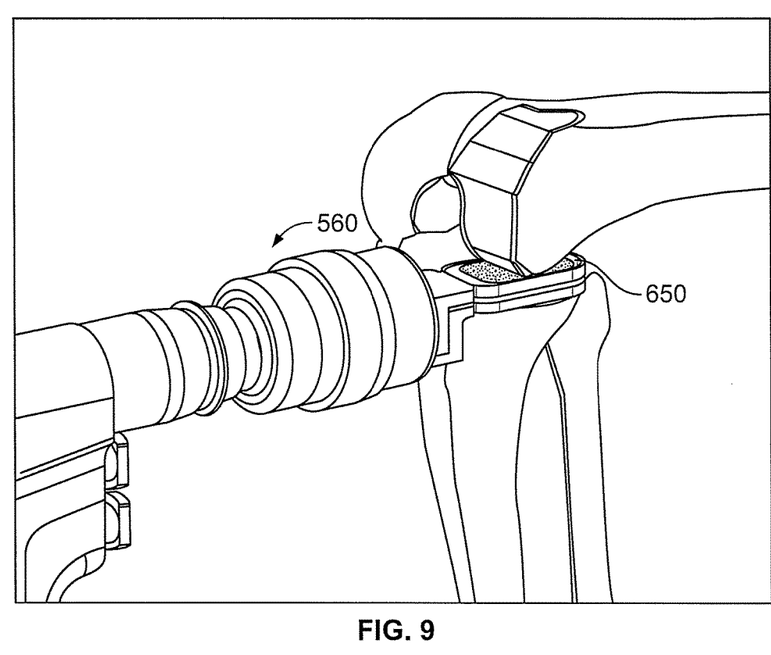
FIG. 9 illustrates a perspective view of the bone removing device arrangement illustrated in FIGS. 7-8 engaged with a resected bone.

In contrast to the bone removing device 100 illustrated in FIGS. 1-4, the bone removing device 560 illustrated in FIG. 7 comprises only one oscillating rasping surface 650 and only one non-oscillating surface 630. Such a bone removing device 650 may be used for a unicompartmental knee arthroplasty where only a portion of the knee is resurfaced, for example, as illustrated in FIG. 9.

It should be understood that the illustrated components are intended as an example only. In other example embodiments, fewer components, additional components, and/or alternative components are possible as well. Further, it should be understood that the above described and shown embodiments of the present disclosure are to be regarded as non-limiting examples and that they can be modified within the scope of the claims.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

We claim:

1. A bone removing device comprising:
    a gearing mechanism,
    a bone removing device housing containing the gearing mechanism,
    a first non-oscillating surface operably connected to the gearing mechanism, and
    a first oscillating rasping surface operably connected to the gearing mechanism,
    wherein, when the gearing mechanism is operated, the first oscillating rasping surface is oscillated within a first plane, and
    wherein a distance between the first plane and the first non-oscillating surface is adjustable.

2. The bone removing device of claim 1, wherein
    the distance between the first plane and the first non-oscillating surface is a manually adjustable distance.

3. The bone removing device of claim 2, further comprising
    a manually operated height adjuster for adjusting the manually adjustable distance between the first non-oscillating surface and the first plane.

4. The bone removing device of claim 3, wherein
    the manually operated height adjuster comprises a twistable outer housing comprising geared teeth on a first end,
    wherein the geared teeth are configured to operate a rack and pinion mechanism so as to increase the distance between the non-oscillating surface and the first plane.

5. The bone removing device of claim 1,
    wherein a proximal end of the bone removing device housing is adapted to receive a surgical instrument.

6. The bone removing device of claim 5,
    wherein the surgical instrument comprises a rotating surgical instrument.

7. The bone removing device of claim 6,
    wherein the rotating surgical instrument is configured to rotate a main drive shaft contained within the bone removing device housing.

8. The bone removing device of claim 7,
    wherein the main drive shaft is connected to a planetary drive system.

9. The bone removing device of claim 8,
    further comprising a sun gear and a main planetary gear,
    wherein the planetary drive system is configured to provide a ratio between the sun gear and the main planetary gear in order to increase revolutions per minute created by the rotating surgical instrument.

10. The bone removing device of claim 9, further comprising
    an intermediate housing containing a vertical beveled gear and a horizontal beveled gear,
    wherein the vertical beveled gear and the horizontal beveled gear are configured to translate a rotational motion into an oscillating linear motion of the first oscillating rasping surface.

11. The bone removing device of claim 10,
    wherein the horizontal beveled gear comprises a protruding peg that engages an oscillating drive shaft.

12. The bone removing device of claim 11,
    wherein the first oscillating rasping surface is removably seated within a cavity defined by a main chassis.

13. The bone removing device of claim 1,
    wherein the first non-oscillating surface comprises an adjustable non-oscillating surface.

14. The bone removing device of claim 13, further comprising:
    a height adjustment knob comprising a geared face.

15. The bone removing device of claim 14, further comprising:
    a spur gear,
    wherein the geared face of the height adjustment knob engages the spur gear and rotation of the height adjustment knob adjusts a distance between
the first non-oscillating surface and
the first oscillating rasping surface.

16. The bone removing device of claim 15, further comprising:
a worm gear drive connected to the spur gear.

17. The bone removing device of claim 1,
wherein the first oscillating rasping surface comprises a plurality of teeth.

18. The bone removing device of claim 1, wherein the bone removing device comprises
a second non-oscillating surface operably connected to the gearing mechanism, and
a second oscillating rasping surface operably connected to the gearing mechanism,
wherein, when the gearing mechanism is operated, the first and the second oscillating rasping surfaces are oscillated.

19. The bone removing device of claim 1,
wherein the first non-oscillating surface comprises a rasping surface.

20. The bone removing device of claim 10,
wherein the oscillating drive shaft is detachably connected to the first oscillating rasping surface.

* * * * *